United States Patent
Stadler et al.

(10) Patent No.: US 9,549,950 B2
(45) Date of Patent: Jan. 24, 2017

(54) CHELATED NANOCERIA FOR THE TREATMENT OF OXIDATIVE STRESS

(71) Applicant: CERION ENTERPRISES, LLC, Rochester, NY (US)

(72) Inventors: Bradford Michael Stadler, Brighton, NY (US); David Wallace Sandford, Rochester, NY (US)

(73) Assignee: CERION, LLC, Rochester, NY (US)

( * ) Notice: Subject to any disclaimer, the term of this patent is extended or adjusted under 35 U.S.C. 154(b) by 113 days.

(21) Appl. No.: 14/261,756

(22) Filed: Apr. 25, 2014

(65) Prior Publication Data

US 2014/0322333 A1    Oct. 30, 2014

Related U.S. Application Data

(60) Provisional application No. 61/854,507, filed on Apr. 25, 2013.

(51) Int. Cl.
| | |
|---|---|
| *A61K 33/24* | (2006.01) |
| *A61K 9/51* | (2006.01) |
| *A61K 47/12* | (2006.01) |
| *A61K 47/18* | (2006.01) |
| *C01F 17/00* | (2006.01) |
| *B82Y 30/00* | (2011.01) |

(52) U.S. Cl.
CPC ............. *A61K 33/24* (2013.01); *A61K 9/5123* (2013.01); *A61K 9/5192* (2013.01); *A61K 47/12* (2013.01); *A61K 47/18* (2013.01); *B82Y 30/00* (2013.01); *C01F 17/0043* (2013.01); *C01P 2002/30* (2013.01); *C01P 2002/76* (2013.01); *C01P 2004/64* (2013.01)

(58) Field of Classification Search
None
See application file for complete search history.

(56) References Cited

U.S. PATENT DOCUMENTS

| | | | | |
|---|---|---|---|---|
| 5,545,386 | A * | 8/1996 | Kaneyoshi ......... | C01F 17/0043 423/263 |
| 7,534,453 | B1 | 5/2009 | Rzigalinski et al. | |
| 8,815,573 | B2 * | 8/2014 | Gorfien ................. | C07K 14/61 435/283.1 |
| 2009/0163639 | A1 * | 6/2009 | Berret .................... | C09D 5/024 524/440 |
| 2010/0172994 | A1 | 7/2010 | Sigmund | |
| 2011/0056123 | A1 * | 3/2011 | Difrancesco .......... | B01F 3/0807 44/410 |
| 2013/0089602 | A1 * | 4/2013 | Boday .................. | A61K 9/1647 424/451 |
| 2013/0337083 | A1 | 12/2013 | Reed et al. | |
| 2013/0337084 | A1 * | 12/2013 | Costanzo ............... | A61K 33/24 424/617 |

FOREIGN PATENT DOCUMENTS

| | | |
|---|---|---|
| EP | 0253 552 A2 | 1/1988 |
| EP | 1 382 570 A1 | 1/2004 |
| EP | 1 726 688 A1 | 11/2006 |
| KR | 2003 0092605 A1 | 12/2003 |
| WO | WO 2007/002662 | 1/2007 |
| WO | WO 2008/030815 | 3/2008 |

OTHER PUBLICATIONS

Xu et al., NPG Asia Materials 6: e90 (2014).*
Rzigalinski in Nanoparticles and Cell Longevity, *Technology in Cancer Research & Treatment* 4(6), 651-659 (2005).
Hardas et al., *Toxicological Sciences* 116(2), 562-576 (2010).
Masui et al., *J. Mater. Sci. Lett.* 21, 489-491 (2002).
Estevez, A.Y., et al., "Neuroprotective mechanisms of cerium oxide nanoparticles in a mouse hippocampal brain slice model of ischemia," Jun. 12, 2011, pp. 1155-1163, vol. 51 (6), Free Radical Biology & Medicine.
International Preliminary Report on Patentability and Written Opinion for International Application No. PCT/US2014/035434 issued Oct. 27, 2015.
International Search Report for PCT/US2014/035454, Issued Oct. 30, 2014.

* cited by examiner

*Primary Examiner* — John Pak
*Assistant Examiner* — Thor Nielsen
(74) *Attorney, Agent, or Firm* — Ratnerprestia

(57) ABSTRACT

A process for making cerium-containing nanoparticles with biocompatible stabilizers is described, wherein an aqueous reaction mixture comprising cerous ion, citric acid, a stabilizer (chelator) selected from the group consisting of nitrilotriacetic acid, ethylene glycol tetraacetic acid and diethylenetriaminepentaacetic acid, and an oxidant, is provided, followed by a heating step to effectively form the nanoparticles. These biocompatible nanoparticles can be used to treat oxidative stress related diseases and events, such as ischemic stroke.

13 Claims, No Drawings

CHELATED NANOCERIA FOR THE TREATMENT OF OXIDATIVE STRESS

CROSS-REFERENCE TO RELATED APPLICATIONS

This patent application claims priority to Provisional Application Ser. No. 61/854,507, STABILIZED NANOCERIA FOR THE TREATMENT OF OXIDATIVE STRESS, filed Apr. 25, 2013, the disclosure of which is incorporated herein by reference in its entirety.

FIELD OF THE INVENTION

The present invention relates in general to improvements in the field of nano-medicine. In particular, the invention relates to cerium-containing nanoparticles prepared with biocompatible materials, to methods of preparing such nanoparticles, and to the use of such nanoparticles to treat disease, such as a neurodegenerative disease, or to treat complications due to oxidative stress arising from, for example, ischemic stroke.

BACKGROUND OF THE INVENTION

Oxidative stress plays a major role in the pathogenesis of many human diseases, and in particular, neurodegenerative diseases. Treatment with antioxidants, which may reduce particular free radical species, therefore, might theoretically prevent tissue damage and improve both survival and neurological outcome. Free radicals in physiological environments can often be classified as either a reactive oxygen species (ROS) or a reactive nitrogen species (RNS). Free radicals are highly reactive chemical species and readily react with proteins, lipids and nucleic acids at a subcellular level and thereby contribute to the progression of various diseases and events producing oxidative stress, such as ischemic stroke.

The origin of the use of nanoceria in nano-medicine can be traced to the seminal work of Bailey and Rzigalinski, wherein the application of ultrafine cerium oxide particles to brain cells in culture was observed to greatly enhanced cell survivability, as described by Rzigalinski in Nanoparticles and Cell Longevity, *Technology in Cancer Research & Treatment* 4(6), 651-659 (2005). More particularly, rat brain cell cultures in vitro were shown to survive approximately 3-4 times longer when treated with 2-10 nanometer (nm) sized cerium oxide nanoparticles synthesized by a reverse micelle micro emulsion technique, as disclosed by Rzigalinski et al. in U.S. Pat. No. 7,534,453, filed Sep. 4, 2003. Cultured brain cells exposed to a lethal dose of free radicals generated by hydrogen peroxide or ultraviolet light exposures were afforded considerable protection by the cerium oxide nanoparticles. In addition, the cerium oxide nanoparticles were reported to be relatively inert in the murine body, with low toxicity (e.g. tail vein injections produced no toxic effects). While no in vivo medical benefits were reported, benefits were postulated for treatments with these ceria nanoparticles, including reduced inflammation associated with wounds, implants, arthritis, joint disease, vascular disease, tissue aging, stroke and traumatic brain injury.

However, a host of problems with these particular nanoceria particles was subsequently disclosed by Rzigalinski et al. in WO 2007/002662. Nanoceria produced by this reverse micelle micro emulsion technique suffered from several problems: (1) particle size was not well-controlled within the reported 2-10 nanometer (nm) range, making variability between batches high; (2) tailing of surfactants, such as sodium bis(ethylhexyl)sulphosuccinate, also known as docusate sodium or (AOT), used in the process into the final product caused toxic responses; (3) inability to control the amount of surfactant tailing posed problems with agglomeration when these nanoparticles were placed in biological media, resulting in reduced efficacy and deliverability; and (4) instability of the valence state of cerium (+3/+4) over time. Thus, the cerium oxide nanoparticles produced by the reverse micelle micro emulsion technique were highly variable from batch to batch, and showed higher than desired toxicity to mammalian cells.

As an alternative, Rzigalinski et al. in WO 2007/002662 describe the biological efficacy of nanoceria synthesized by high temperature techniques, obtained from at least three commercial sources. These new sources of cerium oxide nanoparticles were reported to provide superior reproducibility of activity from batch to batch. It was further reported that, regardless of source, cerium oxide particles having a small size, narrow size distribution, and low agglomeration rate are most advantageous. In regard to size, this disclosure specifically teaches that in embodiments where particles are taken into the interior of cells, the preferable size range of particles that are taken into the cell are from about 11 nm to about 50 nm, such as about 20 nm. In embodiments where particles exert their effects on cells from outside the cells, the preferable size range of these extracellular particles is from about 11 nm to about 500 nm.

These inventors (Rzigalinski et al.) also report that for delivery, the nanoparticles were advantageously in a non-agglomerated form. To accomplish this, they reported that stock solutions of about 10% by weight could be sonicated in ultra-high purity water or in normal saline prepared with ultra-high purity water. However, as others have noted, we have observed that sonicated aqueous dispersions of nanoceria synthesized by high temperature techniques (e.g. obtained from commercial sources) are highly unstable, and settle rapidly (i.e. within minutes), causing substantial variability in administering aqueous dispersions of nanoceria derived from these sources.

Hardas et al., *Toxicological Sciences* 116(2), 562-576 (2010), report on the biodistribution and toxicology effects of aqueous dispersions of nanoceria prepared by the direct two-step hydrothermal preparation of Masui et al., *J. Mater. Sci. Lett.* 21, 489-491 (2002), in which sodium citrate is included as a biocompatible stabilizer. High resolution TEM revealed that this form of nanoceria possessed crystalline polyhedral particle morphology with sharp edges and a narrow size distribution of 4-6 nm. These citrate stabilized ceria nanoparticle dispersions were reported to be stable for more than 2 months at a physiological pH of 7.35. Thus, no sonication prior to administration was required.

Quite surprisingly, however, they report that compared with previously studied commercially sourced nanoceria (Aldrich Chemical Co. (Cat. #639648)), this form of citrate stabilized nanoceria was more toxic, was not seen in the brain, and produced little oxidative stress effect to the hippocampus and cerebellum.

DiFrancesco et al. in commonly assigned PCT/US2007/077545, METHOD OF PREPARING CERIUM DIOXIDE NANOPARTICLES, filed Sep. 4, 2007, describes the oxidation of cerous ion by hydrogen peroxide at low pH (<4.5) in the presence of biocompatible stabilizers, such as citric acid (CA), lactic acid, tartaric acid, gluconic acid, ethylenediaminetetraacetic acid (EDTA), and combinations thereof. Specifically, the stabilizer lactic acid and the combination of lactic acid and EDTA are shown to directly produce stable dispersions of nanoceria of average particle size in the range of 3-8 nm.

Reed et al. in commonly assigned US2013/0337083, NANOCERIA FOR THE TREATMENT OF OXIDATIVE STRESS, filed Mar. 15, 2013, describes a synergistic increase in hippocampal cell sparing for mice treated with nanoceria prepared with a combination of citric acid (CA) and EDTA, wherein the molar ratio of CA/EDTA ranges from 3.0 to 0.1. Amelioration of disease progression and improvement in motor behavior tests resulted in murine models of chronic-progressive multiple sclerosis, relapse-remitting multiple sclerosis, amyotrophic lateral sclerosis and ischemic reperfusion injury.

As described previously, various methods have been reported for preparing biocompatible dispersions of cerium-containing nanoparticles, and in particular those stabilized with citric acid or citrate ion. However, a need remains for further improvement in the free radical scavenging ability of citric acid stabilized cerium-containing nanoparticle dispersions, used, for example, to treat the effects of oxidative stress related diseases and events, such as ischemic stroke.

SUMMARY OF THE INVENTION

In accordance with one aspect of the invention, a process of making a dispersion of nanoparticles is provided, comprising: forming a reaction mixture comprising cerous ion, citric acid, a stabilizer selected from the group consisting of nitrilotriacetic acid, ethylene glycol tetraacetic acid and diethylenetriaminepentaacetic acid, an oxidant, and water; optionally heating or cooling the reaction mixture, and thereby forming a dispersion of cerium-containing nanoparticles in the reaction mixture.

In a second aspect of the invention, a process of treating an oxidative stress related disease or event, such as ischemic stroke, comprising administering before, during or after onset of a disease or event, a cerium-containing nanoparticle prepared in the presence of a mixture of citric acid and a stabilizer selected from the group consisting of nitrilotriacetic acid, ethylene glycol tetraacetic acid and diethylenetriaminepentaacetic acid, is provided.

In a third aspect of the invention, a nanoparticle comprising cerium, citric acid and a stabilizer selected from the group consisting of nitrilotriacetic acid, ethylene glycol tetraacetic acid and diethylenetriaminepentaacetic acid, is provided.

DETAILED DESCRIPTION OF THE INVENTION

It is to be understood that elements not specifically shown or described may take various forms well known to those skilled in the art. The invention is defined by the claims.

In this application, the term nanoparticle includes particles having a mean diameter of less than 100 nm. For the purposes of this disclosure, unless otherwise stated, the diameter of a nanoparticle refers to its hydrodynamic diameter, which is the diameter determined by dynamic light scattering technique and includes molecular adsorbates and the accompanying solvation shell of the particle. Alternatively, the geometric particle diameter can be estimated by analysis of transmission electron micrographs (TEM).

In this application, various cerium-containing materials are nominally described as "cerium oxide" or "cerium dioxide." It is understood by one skilled in the chemical arts, that the actual oxidic anions present in these materials may comprise oxide anions or hydroxide anions, or mixtures thereof, such as hydrated oxide phases (e.g. oxyhydroxide). In addition, it is known that compositions of matter may be comprised of solid solutions of multivalent cations, and are termed non-stoichiometric solids. Thus, for oxide phases comprised of metal cations of multiple oxidation states, it is understood that the total amount of oxidic anions present in a bulk phase will be determined by the specific amounts of the various oxidation states of the metal cations present (e.g. $Ce^{3+}$ and $Ce^{4+}$), such that charge neutrality is maintained. For non-stoichiometric phases nominally described as metal dioxides, this is embodied in the chemical formula $MO_{2-\delta}$, wherein the value of $\delta$ (delta) may vary. For cerium oxides, $CeO_{2-\delta}$, the value of $\delta$ (delta) typically ranges from about 0.0 to about 0.5, the former denoting cerium (IV) oxide, $CeO_2$, the latter denoting cerium (III) oxide, $CeO_{1.5}$ (alternatively denoted $Ce_2O_3$). Alternatively, the value of $\delta$ (delta) denotes the amount of oxygen vacancies present relative to cerium (IV) oxide ($CeO_2$). For each oxygen di-anion vacancy present, two cerous ions ($Ce^{3+}$) are present, to preserve charge neutrality.

In one aspect of the invention, a process of making a dispersion of nanoparticles is provided, comprising: forming a reaction mixture comprising cerous ion, citric acid, a stabilizer (chelator) selected from the group consisting of nitrilotriacetic acid, ethylene glycol tetraacetic acid and diethylenetriaminepentaacetic acid, an oxidant, optionally heating or cooling the reaction mixture, and thereby forming a dispersion of cerium-containing nanoparticles in the reaction mixture.

According to at least one embodiment, the molar ratio of citric acid to the stabilizer may range from about 0.1:0.9 to about 0.9:0.1, such as, for example, from about 0.25:0.75 to about 0.75:0.25, or from about 0.4:0.6 to about 0.6:0.4. In at least one embodiment, the citric acid and stabilizer are present in a molar ratio of about 0.5:0.5.

In one embodiment of the invention, a process of making a dispersion of nanoparticles is provided, comprising: forming a reaction mixture comprising cerous ion, citric acid, a stabilizer selected from the group consisting of nitrilotriacetic acid, ethylene glycol tetraacetic acid and diethylenetriaminepentaacetic acid, an oxidant, and water; optionally heating or cooling the reaction mixture, and directly forming, without isolation of the nanoparticles, a dispersion of cerium-containing nanoparticles in the reaction mixture.

In various embodiments, the oxidant includes compounds more oxidizing than molecular oxygen (or an ambient atmosphere of air). In other embodiments, the oxidant has an aqueous half-cell reduction potential greater than −0.13 volts relative to the standard hydrogen electrode. In at least one embodiment the oxidant is an alkali metal or ammonium perchlorate, chlorate, hypochlorite or persulfate; ozone, a peroxide or a combination thereof. In at least one embodiment, a two-electron oxidant, such as hydrogen peroxide, is used. In accordance with at least one embodiment, hydrogen peroxide is present in an amount greater than one-half the molar amount of cerous ion. In still other embodiments, the amount of oxidant present varies widely in relation to the amount of cerium ions or other metal ions present.

In at least one embodiment, molecular oxygen is passed through the reaction mixture.

In various embodiments, the temperature of the reaction mixture is greater than or less than ambient temperature. In at least one embodiment, the reaction mixture is heated or cooled to temperatures greater than 20° C., or less than or equal to 20° C. In various embodiments, the reaction mixture is heated or cooled to temperatures greater than about 30° C., about 40° C., about 50° C., about 60° C., about 70° C., about 80° C. or about 90° C. In another embodiment, the reaction mixture is heated or cooled to a temperature less than or equal to the boiling temperature of water.

In various embodiments, the nanoparticles formed are amorphous, semi-crystalline or crystalline. As used herein, the term "crystalline," unless otherwise specified, is used to describe nanoparticles having at least some crystalline structure, i.e., either semi-crystalline or crystalline. In at least one embodiment the nanoparticles formed are characterized by a cubic fluorite crystal structure. According to at least one embodiment, the nanoparticles formed are characterized by a cerium oxide crystal structure.

In at least one embodiment, the crystallinity of the nanoparticles formed is enhanced by heating of the reaction mixture.

According to at least one embodiment, the nanoparticles formed are dehydrated or dehydroxylated by heating of the reaction mixture.

In various embodiments, the dispersion of cerium-containing nanoparticles contains substantially non-agglomerated nanoparticles, greater than 90 percent non-agglomerated nanoparticles, greater than 95 percent non-agglomerated nanoparticles, greater than 98 percent non-agglomerated nanoparticles, and entirely non-agglomerated nanoparticles.

In at least one embodiment, the non-agglomerated nanoparticles are crystalline, and are alternatively referred to as single particle crystallites or individual crystallites.

In various embodiments, the nanoparticles formed have a hydrodynamic diameter less than 100 nm, less than 20 nm, less than 10 nm, less than 5.0 nm, less than 3.0 nm or less than about 2.0 nm, while having a hydrodynamic diameter greater than about 1.0 nm.

In at least one embodiment, a nanoparticle comprising cerium is provided. In other embodiments, nanoparticles comprising a cerium oxide, a cerium hydroxide or a cerium oxyhydroxide are provided.

In accordance with at least one embodiment, a nanoparticle comprising cerium, citric acid and a stabilizer selected from the group consisting of nitrilotriacetic acid, ethylene glycol tetraacetic acid and diethylenetriaminepentaacetic acid, is provided.

In various embodiments, the nanoparticle dispersion formed are characterized by a zeta potential ranging from about −30 mV to about +30 mV. In at least one embodiment, the zeta potential of the nanoparticle dispersion ranges from about −15 mV to about −30 mV.

In other embodiments, the zeta potential of the nanoparticle is altered by adjusting the pH of the nanoparticle dispersion, by adjusting the type and amount of stabilizer (e.g. citric acid, nitrilotriacetic acid, ethylene glycol tetraacetic acid or diethylenetriaminepentaacetic acid) content to less than saturation coverage, or both.

In at least one embodiment, the nanoparticle dispersion formed is washed to remove excess ions or by-product salts. In various embodiments, the nanoparticle dispersion is washed such that the ionic conductivity is reduced to less than about 15 millisiemens per centimeter (mS/cm), less than about 10 mS/cm, less than about 5 mS/cm or less than about 3 mS/cm. In various embodiments, the nanoparticle dispersion formed is washed by dialysis or diafiltration.

According to at least one embodiment, the nanoparticle dispersions formed are concentrated to remove excess solvent or excess water. In various embodiments, the nanoparticle dispersion is concentrated by diafiltration or centrifugation.

In various embodiments, the concentration of nanoparticles in the dispersion is greater than about 0.05 molal, greater than about 0.5 molal or greater than about 2.0 molal (approximately 35% solids in a given dispersion).

In various embodiments, the size distributions of the nanoparticles are substantially monomodal. In other embodiments, the nanoparticle size has a coefficient of variation (COV) less than about 30%, less than about 25%, less than about 20%, less than about 15%, less than about 10% or less than about 5%, where the COV is defined as the standard deviation divided by the mean.

In various embodiments, the dispersion of cerium-containing nanoparticles is stable against particle agglomeration and settling, as demonstrated, for example, by maintenance of a clear liquid appearance, for greater than 3 months, greater than 6 months, greater than 9 months, greater than 12 months, and greater than 16 months.

In various embodiments, the reaction mixture is formed in a batch reactor, a continuous reactor or a colloid mill. In at least one embodiment, the continuous reactor is a continuous-stirred-tank reactor or a plug-flow reactor.

In at least one embodiment, mixers can be used to agitate and mix the reactants. In various embodiments, mixers comprising stir bars, marine blade propellers, pitch blade turbines or flat blade turbines are used. In at least one embodiment, a high shear mixer that forces the reaction mixture to pass through a screen, wherein holes vary in size from fractions of a millimeter to several millimeters, is employed.

Physiological pH is typically in the range of about 7.2 to about 7.4.

Without being bound by any theory, the proposed use of cerium oxides for the treatment of inflammation and oxidative stress related diseases (e.g. ROS mediated diseases) is based in part upon a belief that cerium oxides may function as catalytic scavengers of free radicals. The existence of and facile inter-conversion of cerium in a mixture of $Ce^{3+}$ and $Ce^{4+}$ valence states may enable cerium oxides to reduce and/or oxidize free radicals to less harmful species in a catalytic or auto-regenerative manner. Redox reactions may occur on the surface of cerium oxide nanoparticles (CeNPs) that neutralize tissue-damaging free radicals. For example, it is believed to be desirable to oxidize superoxide anion ($O_2-$) to molecular oxygen, to oxidize peroxynitrite anion (ONOO—) to physiologically benign species, and to reduce hydroxyl radical (.OH) to hydroxide anion. This may in turn enable a greatly reduced dosing regimen in comparison to, for example, sacrificial antioxidants currently available to treat oxidative stress related diseases and events.

In at least one embodiment, administered nanoceria particles of the invention are taken into cells through cell membranes and reside in the cellular cytoplasm or in various cellular organelles, such as the nucleus and mitochondria. In other embodiments, the nanoceria particles of the invention reside in intravascular or interstitial spaces, wherein they may reduce oxidative stress and inflammation by eliminating free radicals or reducing autoimmune responses. In at least one embodiment, the immune system invasion of the central nervous system resulting from breakdown of the blood-brain barrier (BBB) or blood-cerebrospinal fluid barrier (BCFB) or blood-ocular barrier (BOB) is modulated by nanoceria particles of the invention.

In another embodiment, the nanoceria particles of the invention are particles capable of crossing a mammalian blood brain barrier. In various embodiments, nanoceria particles of the invention cross a mammalian blood brain barrier and reside in brain parenchyma tissues as aggregates or agglomerates of a size less than about 100 nm, less than about 50 nm, less than about 20 nm, less than about 10 nm, less than about 5 nm. In at least one embodiment, nanoceria particles of the invention cross a mammalian blood brain barrier and reside in brain parenchyma tissues as independent, non-agglomerated nanoparticles of a size less than about 3.5 nm.

In at least one embodiment, a pharmaceutical composition comprising nanoceria particles of the invention are specifically contemplated for prevention and/or treatment of oxidative stress related diseases and events, such as, but not limited to, Alzheimer's Disease, Parkinson's Disease, Huntington's Disease, amyotrophic lateral sclerosis (ALS), ataxia, Friedreich's ataxia, autism, obsessive-compulsive disorder, attention deficit hyperactivity disorder, migraine, stroke, traumatic brain injury, cancer, inflammation, autoimmune disorders, lupus, multiple sclerosis (MS), inflammatory bowel disease, Crohn's Disease, ulcerative colitis, stenosis, restenosis, atherosclerosis, metabolic syndrome, endothelial dysfunction, vasospasms, diabetes, aging, chronic fatigue, coronary heart disease, cardiac fibrosis, myocardial infarction, hypertension, angina, Prizmetal's angina, ischemia, angioplasty, hypoxia, Keshan disease, glucose-6-phosphate dehydrogenase deficiency, favism, ischemic reperfusion injury, rheumatoid and osteo-arthritis, asthma, chronic obstructive pulmonary disease (e.g. emphysema and bronchitis), allergies, acute respiratory distress syndrome, chronic kidney disease, renal graft, nephritis, ionizing radiation damage, sunburn, dermatitis, melanoma, psoriasis, macular degeneration, retinal degeneration, cataractogenesis, among others.

In accordance with various embodiments, a pharmaceutical composition comprising nanoceria particles of the invention are specifically contemplated for prevention and/or treatment of oxidative stress related cellular pathologies, such as, but not limited to, mitochondrial dysfunction, lysosome and proteasome dysfunction, oxidation of nucleic acids (e.g. RNA and DNA), tyrosine nitration, loss of phosphorylation mediated signaling cascades, initiation of apoptosis, lipid peroxidation and destruction of the membrane lipid environment.

In various embodiments, a pharmaceutical composition comprising nanoceria particles of the invention is administered to a human or a non-human subject, such as another mammal, including, but not limited to, a canine, a feline, a bovine, an equine, an ovine, a porcine or a rodent. Alternatively, the subject of administration can be an animal such as a bird, insect, reptile, amphibian, or any companion or agricultural animal.

In various embodiments, nanoceria particles of the invention are administered in vivo to a subject by topical, enteral or parenteral methods, including injections, infusions or implantations. More particularly, it is specifically contemplated to administer nanoceria particles of the invention by any of the following routes: auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intraabdominal, intra-amniotic, intra-arterial, intrabiliary, intrabronchial, intrabursal, intracardiac, intracartilaginous, intracaudal, intracavernous, intracavitary, intracerebral, intracisternal, intracorneal, intracornal-dental, intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmammary, transmucosal, transplacenta, transtracheal, transtympanic, ureteral, urethral, vaginal, and any other or unassigned route.

In other embodiments, nanoceria particles of the invention are retained in or on the surface of a medical device or prosthesis, such as a cannula, catheter or stent, thereby reducing inflammation locally or systemically, over either a short or long time period.

In various embodiments, the nanoceria particles of the invention are delivered in any suitable form known in the art, including, but not limited to, a suspension, gel, tablet, enteric coated tablet, loaded liposome, powder, suppository, infusible, lozenge, cream, lotion, salve, or inhalant.

In various embodiments, the nanoceria particles of the invention are combined with other pharmaceutically acceptable substances, such as, but not limited to, water, salts, buffers, phosphate buffered saline (PBS), sugars, human or bovine serum albumen, lipids, drugs, colorants, flavorants, binders, gums, surfactants, fillers or any excipients known in the art.

In at least one embodiment, the vehicle comprising the nanoceria particles of the invention is sterilized prior to administration.

In other embodiments, a cell or cell culture is contacted with a nanoceria particle or particles of the invention. Contact may be practiced by exposing a cell or cell culture by in vitro or ex vivo methods, wherein the latter method comprises re-introducing the treated cell or cells into a subject, such as the subject from which the cell or cells were originally obtained. In various embodiments the cell is prokaryotic or eukaryotic in nature. In at least one embodiment, the treated cells are used in the production of proteins used in the pharmaceutical industry, generally known as biologics, such as, but not limited to, antigens, antibodies and vaccines. In another embodiment, the treated cells are used in a fermentation process.

The invention is further illustrated by the following examples, which are not intended to limit the invention in any manner.

EXPERIMENTAL SECTION

Nanoparticle Scattering and Size Assessments

A simple qualitative characterization of the particle dispersions was performed by assessing the degree of Tyndell scattering exhibited by the dispersions when illuminated by a red laser pen light, relative to the amount of scattering from a sample of the neat solvent. A quantitative assessment of the particle size of the nanoparticle dispersions was performed by dynamic light scattering (DLS) using a Brookhaven 90Plus Particle Size Analyzer (Brookhaven Instruments Corp., Holtzville, N.Y., U.S.A.) equipped with a quartz cuvette. Reported DLS sizes are the lognormal number weighted parameter.

Nanoparticle Charge Assessment

A quantitative assessment of the nanoparticle charge was made by measuring the zeta potential using a Zetasizer Nano ZS from Malvern Instruments.

Example 1

Preparation of Nanoparticles with Cerium and Citric Acid

Into a 800 ml glass beaker containing a magnetic stir bar was introduced 500 ml of high purity (HP) water. The water was then heated to about 70° C., and therein 4.83 grams of citric acid (CA) were dissolved. Ammonium hydroxide (28-30%) was added to adjust the pH of the solution to about 8.5. The temperature of the reaction vessel was raised to about 80° C. A 10.0 gm quantity of $Ce(NO_3)_3.6(H_2O)$ was dissolved in 30 ml of HP water, and this solution was added slowly to the stirred reaction mixture over several minutes. In this way, equimolar amounts of CA and Ce had been added to the reaction mixture. Then a 50 ml solution containing 4.8 ml of 50% $H_2O_2$ (3.0 molar ratio of $H_2O_2$ to cerium) was added slowly over several minutes to the equimolar reaction mixture of cerous ion and citric acid. The reaction product was covered and then heated for an additional hour, resulting in a clear yellow suspension. After cooling with stirring, the directly formed nanoparticle dispersion was washed by diafiltration to an ionic conductivity of less than about 10 mS/cm, to remove excess salts.

The final product dispersion was a clear yellow liquid that displayed a high degree of Tyndall scattering when illuminated with a low intensity LASER beam, indicating it contained well-dispersed colloidal particles. Particle size analysis by dynamic light scattering indicated an average hydrodynamic diameter of 7.8 nm. Analysis of a X-ray diffraction (XRD) spectrum indicated the presence of a major crystalline phase iso-structural with $CeO_2$ (PDF #34-394, cerianite) characterized by a cubic fluorite structure. An average crystallite size of 2.0 nm was determined by analysis of the (220) peak width using the Scherrer method.

Example 2

Preparation of Nanoparticles with Cerium, Citric Acid and DCTA

Into a 600 ml glass beaker containing a magnetic stir bar was introduced 500 ml of high purity (HP) water. A 2.41 gm quantity of citric acid (CA) was added to the reaction mixture. A 4.264 gm quantity of 1,2-Diaminocyclohexanetetraacetic acid monohydrate (DCTA) was dissolved in water along with about 6 ml of ammonium hydroxide to aid in dissolution, and added to the reaction mixture. Ammonium hydroxide (28-30%) was added to adjust the pH of the solution to about 8.5. A 10.0 gm quantity of $Ce(NO_3)_3.6(H_2O)$ was added. The molar proportions of CA/DCTA/Ce were 0.5/0.5/1.0. Then a 10 ml solution containing 4.8 gm of 50% $H_2O_2$ (3.0 molar ratio of $H_2O_2$ to cerium ion) was added slowly to the cerium, citric acid and DCTA solution mixture. The reaction product was then heated at 80° C. for 1 hour. After cooling with stirring, the directly formed nanoparticle dispersion was washed by diafiltration to an ionic conductivity of less than about 10 mS/cm, to remove excess salts.

After cooling, the final product dispersion was a clear light orange colored liquid that displayed a high degree of Tyndall scattering when illuminated with a low intensity LASER beam, indicating it contained well-dispersed colloidal particles. Particle size analysis by dynamic light scattering indicated a hydrodynamic diameter of 2.6 nm with a polydispersity of 0.227. Analysis of a X-ray diffraction (XRD) spectrum indicated the presence of a major crystalline phase iso-structural with $CeO_2$ (PDF #34-394, cerianite) characterized by a cubic fluorite structure. An average crystallite size of 1.9 nm was determined by analysis of the (220) peak width using the Scherrer method.

Example 3

Preparation of Nanoparticles with Cerium, Citric Acid and NTA

Into a 600 ml glass beaker containing a magnetic stir bar was introduced 500 ml of high purity (HP) water. A 2.41 gm quantity of citric acid (CA) was added to the reaction mixture. A 3.129 gm quantity of 2,2',2''-Nitrilotriacetic acid (NTA, CAS No. 139-13-9) was dissolved in water along with ammonium hydroxide to aid in dissolution, and added to the reaction mixture. Ammonium hydroxide (28-30%) was added to adjust the pH of the solution to about 8.5. A 10.0 gm quantity of $Ce(NO_3)_3.6(H_2O)$ was added. The molar proportions of CA/NTA/Ce were 0.5/0.5/1.0. Then a 10 ml solution containing 4.8 gm of 50% $H_2O_2$ (3.0 molar ratio of $H_2O_2$ to cerium ion) was added slowly to the cerium, citric acid and NTA solution mixture. The reaction product was then heated at 80° C. for 1 hour. After cooling with stirring, the directly formed nanoparticle dispersion was washed by diafiltration to an ionic conductivity of less than about 10 mS/cm, to remove excess salts.

The final product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 2.8 nm with a polydispersity of 0.264.

Example 4

Preparation of Nanoparticles with Cerium, Citric Acid and EGTA

Into a 600 ml glass beaker containing a magnetic stir bar was introduced 500 ml of high purity (HP) water. A 2.41 gm quantity of citric acid (CA) was added to the reaction mixture. A 4.497 gm quantity of Ethylene Glycol Tetraacetic acid (EGTA, CAS No. 67-42-5) was dissolved in water along with ammonium hydroxide to aid in dissolution, and added to the reaction mixture. Ammonium hydroxide (28-30%) was added to adjust the pH of the solution to about 8.5. A 10.0 gm quantity of $Ce(NO_3)_3.6(H_2O)$ was added. The molar proportions of CA/EGTA/Ce were 0.5/0.5/1.0. Then a 10 ml solution containing 4.8 gm of 50% $H_2O_2$ (3.0 molar ratio of $H_2O_2$ to cerium ion) was added slowly to the cerium, citric acid and EGTA solution mixture. The reaction product was then heated at 70° C. for 1 hour. After cooling with stirring, the directly formed nanoparticle dispersion was washed by diafiltration to an ionic conductivity of less than about 10 mS/cm, to remove excess salts.

The final product dispersion was a clear orange liquid that displayed a high degree of Tyndall scattering when illuminated with a low intensity LASER beam, indicating it contained well-dispersed colloidal particles. Particle size analysis by dynamic light scattering indicated a hydrodynamic diameter of 8.5 nm with a polydispersity of 0.393.

Example 5

Preparation of Nanoparticles with Cerium, Citric Acid and DTPA

Into a 600 ml glass beaker containing a magnetic stir bar was introduced 500 ml of high purity (HP) water. A 2.89 gm quantity of citric acid (CA) was added to the reaction mixture. A 3.606 gm quantity of Diethylenetriaminepentaacetic acid (DTPA, CAS No. 67-43-6) was added to the reaction mixture. Ammonium hydroxide (28-30%) was added to adjust the pH of the solution to about 8.5. A 10.0 gm quantity of $Ce(NO_3)_3.6(H_2O)$ was added. The molar proportions of CA/DTPA/Ce were 0.6/0.4/1.0. Then a 10 ml solution containing 4.8 gm of 50% $H_2O_2$ (3.0 molar ratio of $H_2O_2$ to cerium ion) was added slowly to the cerium, citric acid and DTPA solution mixture. The reaction product was then heated at 80° C. for 1 hour. After cooling with stirring, the directly formed nanoparticle dispersion was washed by diafiltration to an ionic conductivity of less than about 10 mS/cm, to remove excess salts.

The final product dispersion was a clear red liquid that displayed a high degree of Tyndall scattering when illuminated with a low intensity LASER beam, indicating it contained well-dispersed colloidal particles. Particle size analysis by dynamic light scattering indicated a hydrodynamic diameter of 2.4 nm with a polydispersity of 0.212. Analysis of a X-ray diffraction (XRD) spectrum indicated the presence of a major crystalline phase iso-structural with $CeO_2$ (PDF #34-394, cerianite) characterized by a cubic fluorite structure. An average crystallite size of 2.1 nm was determined by analysis of the (220) peak width using the Scherrer method.

A sample of the final product dispersion was stored in the dark at ambient temperature and pressure for a time period greater than 16 months with no change in the clarity of the liquid and no change in particle hydrodynamic diameter and polydispersity.

Evaluation of Stabilized Nanoceria in a Murine Model of Ischemic Stroke

The ability of cerium-containing nanoparticles (e.g. nanoceria) to reduce oxidative stress was evaluated in a modification of the in vitro mouse hippocampal brain slice model of ischemia described by Estevez, A Y; et al., Neuroprotective mechanisms of cerium oxide nanoparticles in a mouse hippocampal brain slice model of ischemia, *Free Radic. Biol. Med.* (2011)51(6):1155-63 (doi:10.1016/j.radbiomed.2011.06.006).

Adult (2-5 months of age) CD1 mice were sacrificed via rapid decapitation and their brains quickly removed and placed in a chilled choline-based slicing solution containing 24 mM choline bicarbonate, 135 mM choline chloride, 1 mM kynurenic acid, 0.5 mM $CaCl_2$, 1.4 mM $Na_2PO_4$, 10 mM glucose, 1 mM KCl, and 20 mM $MgCl_2$ (315 mOsm). Transverse hippocampal slices, 400 μm thick, were cut along a rostral-to-caudal axis (−1.2 to −2.8 mm Bregma) using a Leica VT1200 Vibratome (Leica Microsystems, Wetzlar, Germany) and allowed to recover for 1 hr in a control artificial cerebral spinal fluid (aCSF) containing 124 mM NaCl, 3 mM KCl, 2.4 mM $CaCl_2$, 1.3 mM $MgSO_4$, 1.24 mM $K_3PO_4$, 26 mM $NaHCO_3$, 10 mM glucose and bubbled with 5% $CO_2$, 95% $O_2$ gas (pH 7.4, 300 mOsm). Hippocampal slices were placed in a culture dish and stored in a NuAire humidified incubator (NuAire, Plymouth, Minn., USA) at 37° C. with 5% $CO_2$ for up to 48 hr.

Oxidative stress from ischemia was induced by placing the brain slices in hypoglycemic, acidic and hypoxic aCSF (glucose and pH were lowered to 2 mM and 6.8, respectively, and the solution was bubbled with 84% $N_2$, 15% $CO_2$, and 1% $O_2$) at 37° C. for 30 min. Sucrose was added to maintain the osmolarity of the solution at about 295 mOsm.

Aqueous dispersions of cerium-containing nanoparticles prepared as described in Examples 1-5 supra were administered in matched dosage in a delivery volume of 1 μg per 1 ml aCSF or medium (equivalent to 5.8 μM) at the onset of the ischemic event, and remained in the medium throughout the remainder of the experiment. Control slices received an equal volume of vehicle control. Various delivery vehicles were used with similar success for the cerium oxide nanoparticles prepared as described herein, including distilled water alone, saline solution, Na-citrate solution, PBS, and combinations thereof.

After exposure to 30 minutes of oxidative stress (ischemic conditions), the living brain slices (test and control) were incubated for 24 hr in organotypic culture by placing them in a 35 mm culture dish containing culture medium and Millipore inserts (Millipore, Billerica, Mass., USA). Culture medium contained 50% minimum essential medium (Hyclone Scientific, Logan Utah, USA), 25% horse serum, 25% Hank's balanced salt solution (supplemented with 28 mM glucose, 20 mM HEPES and 4 mM $NaHCO_3$), 50 U/ml penicillin, and 50 μl/ml streptomycin, pH 7.2.

The extent of cell death was measured 24 hours after the oxidative injury using fluorescence imaging techniques. Each set of brain slices studied in the test condition (i.e. administered with cerium-containing nanoparticles) was matched with a similar set of control brain slices treated identically in every way except for administration of vehicle alone. Thus on each study day, two sets of anatomically matched brain slices taken from age-matched and sex-matched littermates were subjected to either the test condition (administered with cerium-containing nanoparticles) or control (vehicle alone). During fluorescence imaging measurements, the light intensity, duration of image capture, and timing of image collection were identical for the test condition and vehicle control brain slices. Results were expressed as the ratio of the fluorescence in the test condition to the fluorescence in the matched control slice imaged at the same time point in the experimental sequence.

At 24 hours post oxidative injury, paired (control and test) brain slices were incubated for 20 min in culture medium containing 0.81 μM vital exclusion dye SYTOX® Green (Invitrogen, Carlbad, Calif., USA) and, subsequently, washed for 15-20 min in culture medium to remove unincorporated dye. SYTOX® Green is a fluorescent dye that binds to DNA and RNA. However, it is excluded from the cell nucleus by the cell membrane in intact, viable cells. Therefore, it acts as a vital dye and stains only those dead and dying cells in which the cell membrane has become permeable so that the dye has access to the cell interior. After staining and washing, brain slices were transferred to the stage of a Nikon TE 2000-U (Nikon Instruments, Melville, N.Y., USA) microscope equipped with epifluoresence attachments and a 150-W xenon light source (Optiquip, Highland Mills, N.Y., USA). Control aCSF solution was loaded into 60-ml syringes, equilibrated with 95% $O_2$/5% $CO_2$, and heated to 37° C. using a servo-controlled syringe heater block, stage heater, and in-line perfusion heater (Warner Instruments, Hamden, Conn., USA). The brain sections were continuously perfused with warmed, 95%

$O_2$/5% $CO_2$ equilibrated aCSF at a rate of 1 ml per minute. After 5 min, images of the hippocampal formation of each control and test brain slice were collected using a 4× Plan Flour objective (Nikon Instruments) under identical conditions (i.e. light intensity, exposure time, camera acquisition parameters). SYTOX® Green fluorescence was measured by briefly (620 ms) exciting the tissue at 480±40 nm, filtering the emitted fluorescence (535±50 nm) from the probe using a 505 nm, long-pass, dichroic mirror (Chroma technology, Bennington, Vt., USA), intensifying, and measuring with a cooled CCD gain EM camera (Hamamatsu CCD EM C9100; Bridgewater, N.J., USA). The digital images were acquired and processed with Compix SimplePCI 6.5 software (C Imaging Systems, Cranberry Township, Pa., USA).

The light intensity resulting from the SYTOX® Green loading reflected the number of dead or dying cells within the calculated area. The light-intensity measurements were performed automatically using the Compix SimplePCI 6.5 software, thereby eliminating experimenter bias in selecting the regions of interest.

Reduction in cell death is reported as the ratio of the light intensity of SYTOX® Green fluorescence from the cornu ammonis fields (oriens layer, stratum radiatum and lacunosum moleculare) for the test condition (i.e. nanoceria treated) to the control (untreated) for anatomically matched hippocampal sections taken from age-matched and sex-matched littermate brains sliced and exposed to ischemic oxidative stress on the same day, and fluorescence imaged 24 hr after the ischemic insult.

Cerium-containing nanoparticles prepared with citric acid stabilizer alone, and with a mixture of biocompatible stabilizers comprising citric acid and one of DCTA, NTA, EGTA or DTPA, prepared as described in Example 1-5, were evaluated in the mouse hippocampal brain slice model of ischemic stroke using a treatment concentration of 5.8 μM. Results for the reduction in cell death (percent reduction relative to control), commonly referred to as sparing, as a function of nanoparticle stabilizer are given in Table 1 below.

TABLE 1

| Source of Nanoparticles | Stabilizer(s) | DLS (nm) | Sparing | Comment |
|---|---|---|---|---|
| Ex. 1 | CA | 7.8 | 15.5% | Comparative |
| Ex. 2 | CA/DCTA | 2.6 | 14.2% | Comparative |
| Ex. 3 | CA/NTA | 2.8 | 17.0% | Inventive |
| Ex. 4 | CA/EGTA | 8.5 | 23.3% | Inventive |
| Ex. 5 | CA/DTPA | 2.4 | 34.0% | Inventive |

Results shown in Table 1 above indicate that an improvement in sparing (i.e. a greater reduction in cell death) occurred when the cerium-containing nanoparticles were prepared with a combination of citric acid (CA) and either NTA, EGTA or DTPA.

While the invention has been described by reference to various specific embodiments, it should be understood that numerous changes may be made within the spirit and scope of the inventive concepts described. Accordingly, it is intended that the invention not be limited to the described embodiments, but will have full scope defined by the claims.

We claim:

1. A method of making a dispersion of nanoparticles, comprising:
   a. forming a reaction mixture comprising cerous ion, citric acid, a stabilizer, an oxidant, and water, wherein the stabilizer is selected from the group consisting of nitrilotriacetic acid, ethylene glycol tetraacetic acid and diethylenetriaminepentaacetic acid; and
   b. forming a dispersion of cerium-containing nanoparticles in the reaction mixture.

2. The method of claim 1, further comprising heating or cooling the reaction mixture.

3. The method of claim 1, wherein the temperature of said reaction mixture is less than or equal to the boiling temperature of water.

4. The method of claim 1, wherein said cerium-containing nanoparticles comprise an oxide of cerium.

5. The method of claim 1, wherein said cerium-containing nanoparticles are crystalline.

6. The method of claim 5, wherein said nanoparticles are characterized by a cubic fluorite crystal structure.

7. The method of claim 1, wherein said oxidant comprises hydrogen peroxide.

8. The method of claim 1, wherein said cerium-containing nanoparticles are substantially non-agglomerated.

9. The method of claim 1, wherein said dispersion of cerium-containing nanoparticles is stable against particle agglomeration and settling for greater than 12 months.

10. The method of claim 1, wherein said dispersion of cerium-containing nanoparticles is stable against particle agglomeration and settling for about 12 months.

11. The method of claim 1, wherein said dispersion of cerium-containing nanoparticles has a zeta-potential ranging from about −15 mV to about −30 mV.

12. The method of claim 1, wherein said cerium-containing nanoparticles are characterized by a hydrodynamic diameter less than 10 nanometers.

13. The method of claim 1, wherein said cerium-containing nanoparticles are characterized by a hydrodynamic diameter of about 10 nanometers.

\* \* \* \* \*